United States Patent [19]
Yamada et al.

[11] Patent Number: 6,005,105
[45] Date of Patent: Dec. 21, 1999

[54] PROCESS FOR PRODUCING IMIDAZOLE DERIVATIVE

[75] Inventors: Hiroyoshi Yamada, Tsukuba; Kiyotaka Munesada, Shimotsuma; Keiko Koh, Tsukuba; Kazuo Tsuzuki, Tsukuba; Mikio Taniguchi, Tsukuba; Yoshiji Fujita, Abiko, all of Japan

[73] Assignee: Pharmacia & Upjohn Company, Kalamazoo, Mich.

[21] Appl. No.: 08/557,072

[22] PCT Filed: Jun. 2, 1994

[86] PCT No.: PCT/US94/06028

§ 371 Date: Dec. 6, 1995

§ 102(e) Date: Dec. 6, 1995

[87] PCT Pub. No.: WO95/00517

PCT Pub. Date: Jan. 5, 1995

[30] Foreign Application Priority Data

Jun. 21, 1993 [JP] Japan ................................ 5-149132

[51] Int. Cl.$^6$ ................................................ C07D 487/18
[52] U.S. Cl. ............................................ 544/233; 548/250
[58] Field of Search ............................. 544/233; 548/250

[56] References Cited

U.S. PATENT DOCUMENTS

| | | | |
|---|---|---|---|
| 5,039,814 | 8/1991 | Shuman et al. | 548/250 |
| 5,252,753 | 10/1993 | Russell et al. | 548/250 |
| 5,405,960 | 4/1995 | Chekroun et al. | 548/250 |
| 5,442,062 | 8/1995 | Koh et al. | 544/234 |
| 5,468,867 | 11/1995 | Fisher et al. | 548/250 |

FOREIGN PATENT DOCUMENTS 0 540 209 A1  5/1993  European Pat. Off. .

*Primary Examiner*—Emily Bernhardt
*Attorney, Agent, or Firm*—Lawrence T. Welch; Ruth H. Newtson

[57] ABSTRACT

The present invention is directed to a process for preparing the following compound

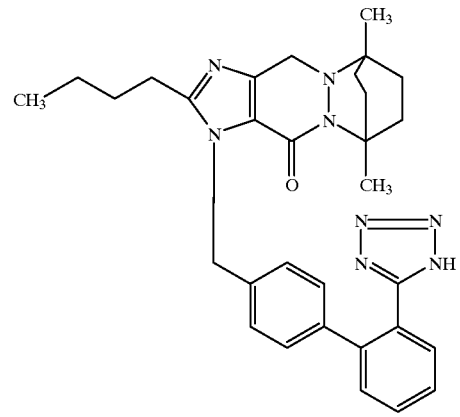

which is prepared starting from

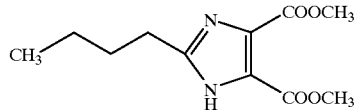

which is reacted succesively with 4-iodobenzyl or 4-bromobenzyl bromide, hydrazine and 1,4-dimethyl-1,3-cyclohexadiene, reduced and reacted with phenyltetrazole or suitably protected phenyltetrazole followed by removal

2 Claims, No Drawings

PROCESS FOR PRODUCING IMIDAZOLE DERIVATIVE

This application is the national phase of international application PCT/US94/06028, filed Jun. 21, 1993 which claims the priorty of Japanese Application No. 149132/1993, filed Jun. 21, 1993.

BACKGROUND
Industrial Field of Utilization

The present invention relates to a process for producing an imidazole derivative. More particularly, it relates to a process for producing an imidazole derivative represented by the chemical formula [I]:

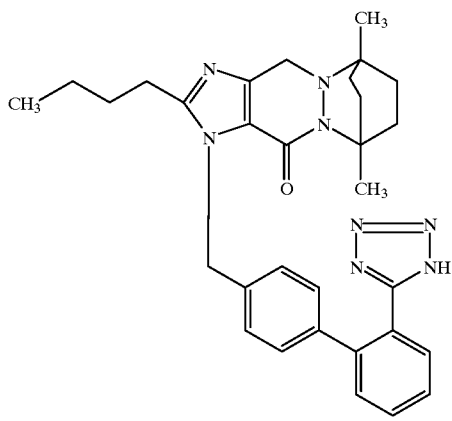

which is useful for hypertension, congestive heart failure, renal failure, glaucoma, hyperuricemia and the like, in which complicated steps are avoided.

The above compound is an angiotensin II antagonist and is thus useful as an agent for preventing or treating hypertension, congestive heart failure, renal failure, glaucoma, hyperuricemia and the like. The present inventors have found that drugs of this class have longer shelf life, higher activity, rapid manifestation of action upon intravenous injection, good absorbability into the body upon oral administration, lower toxicity and long-lasting action. These novel compounds are imidazole derivatives having the hydrazine cross-linking structure represented by the formula:

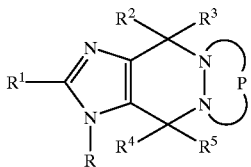

as described in Japanese Patent Application No. 3-277537, No. 3-323474, No. 4-095191 and No. 4-216809 and published PCT application WO 93/08193, published Apr. 29, 1993, which claims the benefit thereof. In the above applications, we reported the imidazole derivative [I] represented by the chemical formula:

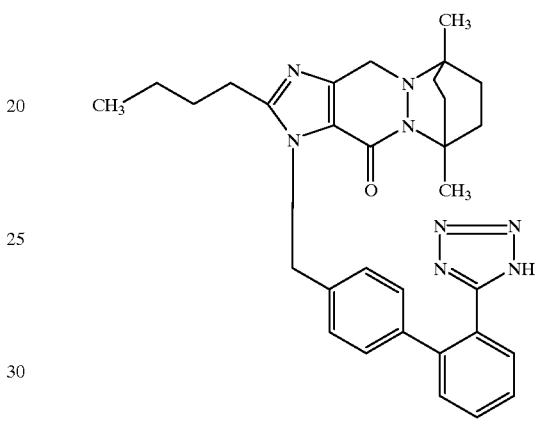

had particularly good effects. And we disclosed, in the above patent applications and Japanese Patent Application No. 5-060067, that this imidazole derivative can be synthesized according to the following route (Reaction scheme 1). In the route, a compound (1) is first protected with benzyl group, and after a few steps, the protected compound is debenzylated by hydrogenolysis to give a compound (4) and thereafter, a biphenyltetrazole part is linked thereto to give an end compound [I]. However, the above route has the problems in production efficacy and economical properties. In this regard, Richard F. Shuman et al. reported an improved process for producing biphenyltetrazoles which are an intermediate useful for production of angiotensin II antagonist in U.S. Pat. No. 5,039,814.

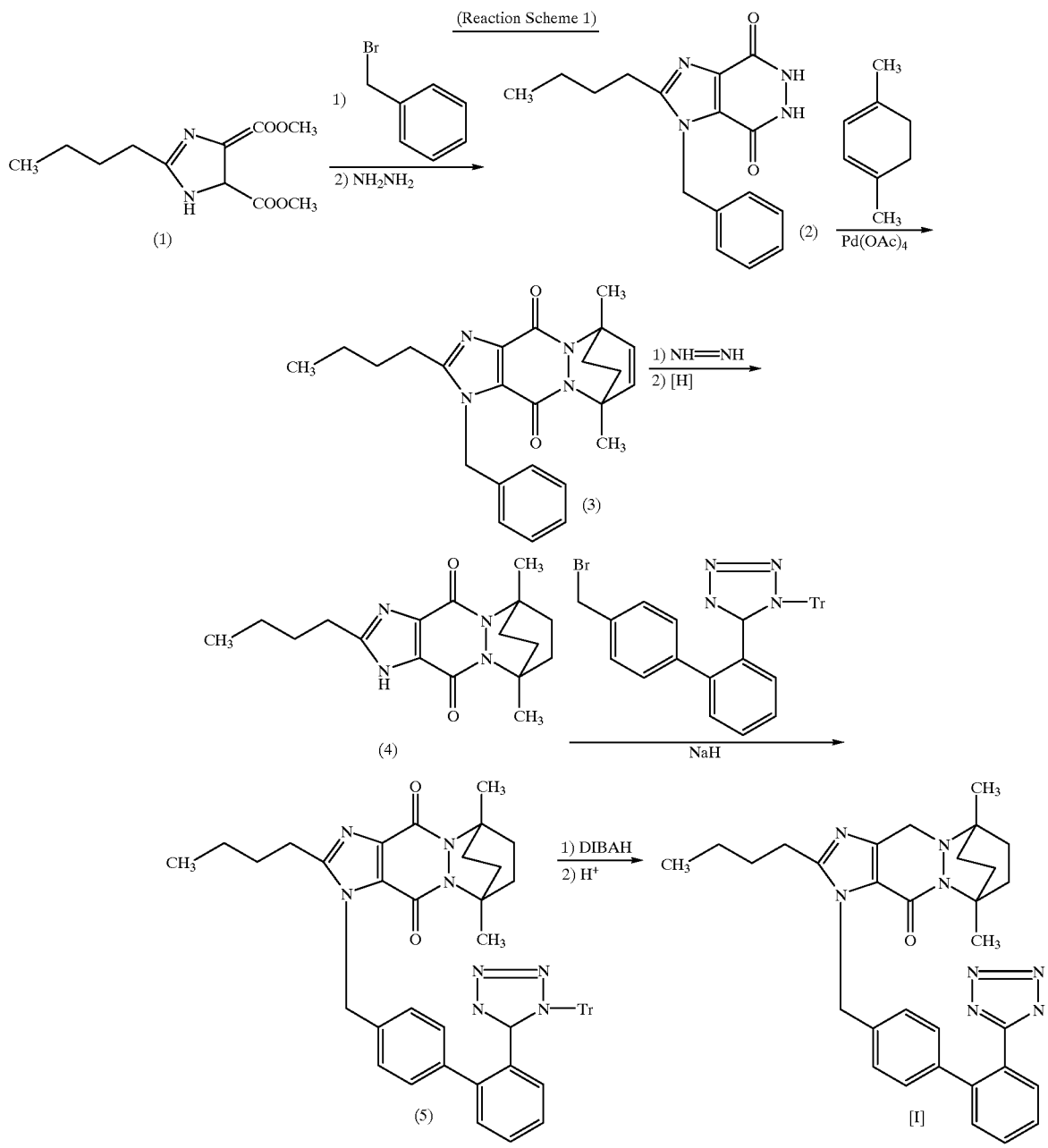

(Reaction Scheme 1)

INFORMATION DISCLOSURE

Methods of synthesis of compounds of the formula I are described in WO 93/08193, published Apr. 29, 1993. Another process is discussed in U.S. Pat. No. 5,039,814.

SUMMARY OF THE INVENTION

Problems to be Solved by the Invention

The object of the present invention is to provide a process for producing an imidazole derivative having the excellent effects without passing through the complicated synthesis route.

The present inventors have studied the problems and have found that the imidazole compound can be prepared without passing through a reaction of deprotecting the benzyl group by introducing therein a p-halogenobenzyl group, which resulted in completion of the present invention.

That is, the present invention provides a process for producing an end compound [I] (Process A) which comprises introducing p-halogenobenzyl group in the compound (1) in place of protecting the compound (1) with benzyl group, subjecting the protected compound to the following route (Reaction Scheme 2) to give a compound (8), subjecting the resulting compound to cross-coupling with phenyltetrazole or suitably protected phenyltetrazole to construct a biphenyltetrazole part, and subjecting the resulting compound to diisobutylaluminium hydride (DIBAH) reduction, and a process for producing an end compound [I] (Process B) which comprises subjecting a compound (8) to diisobutylaluminium hydride reduction to give a compound (9), subjecting it to cross-coupling with phenyltetrazole or suitably protected phenyltetrazole to construct a biphenyltetrazole part. These processes do not need the complicated procedures such as protection with benzyl group, deprotection, synthesis of biphenyltetrazole, reaction with imidazole and the like. Further these processes have the advantages such that all the reactions are utilized effectively for construction of an end compound and respective steps have the higher yield.

like, said aryl being optionally substituted with lower alkyl group such as methyl, ethyl and the like or lower alkoxy group such as methoxy, ethoxy and the like.

Regarding the cross-coupling reaction used in the present invention, there is known a process for production of 2-substituted-1-(tetrazol-5-yl)benzenes disclosed in U.S. Pat. No. 5039814 (Reaction Scheme 3). However, this disclosure relates to a process for production of an intermediate (12) which is a biphenyltetrazole part and reports as R

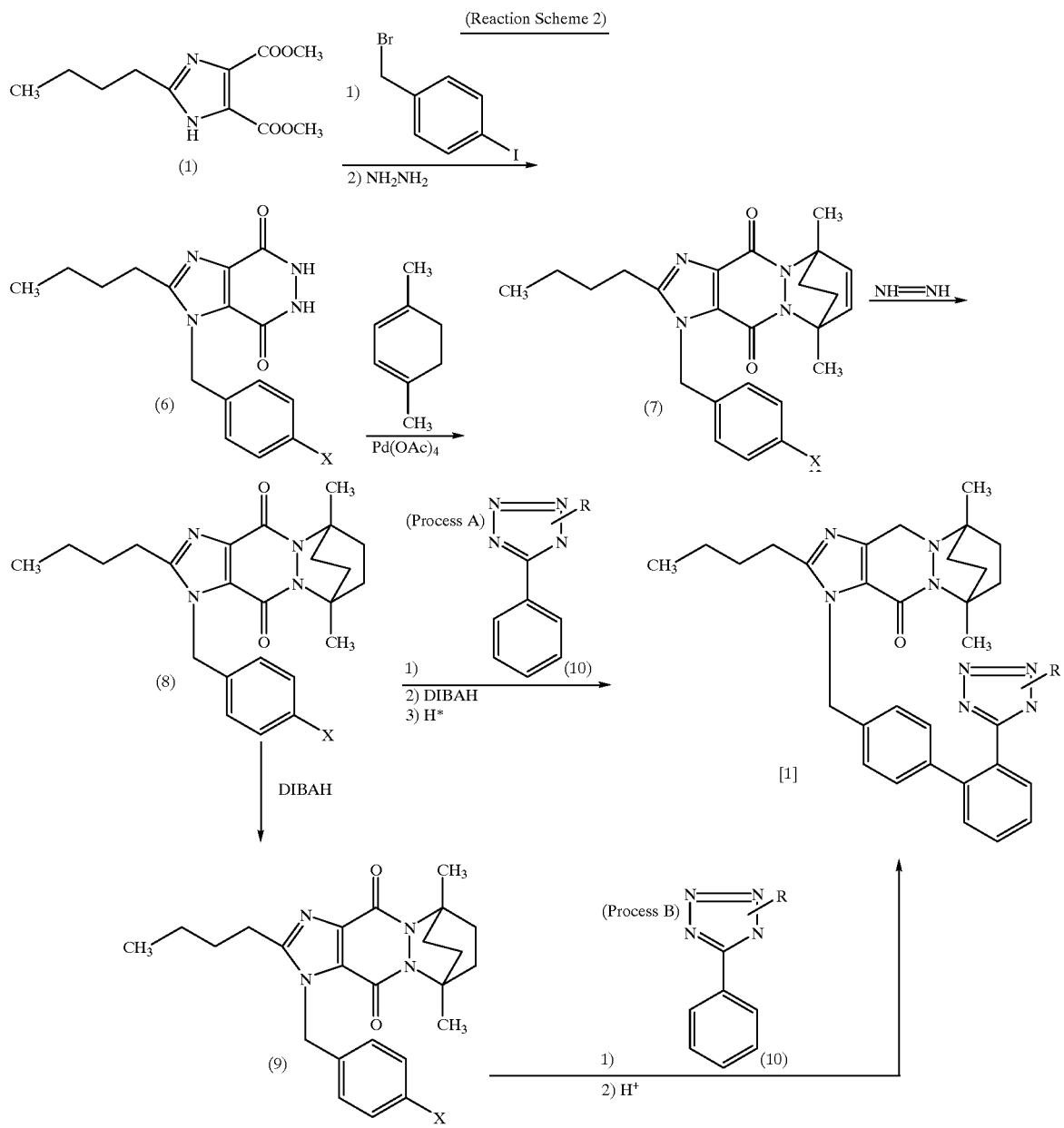

As the alkyl group represented by a variable substituent R, there are methoxymethyl, methoxyethoxymethyl, trimethylsilylethoxymethyl and the like. As the optionally substituted aryl group, there are benzyl, diphenylmethyl, triphenylmethyl, naphthylmethyl, 9-anthrylmethyl and the group on phenyltetrazole (11) only hydrogen and triphenylmethyl group. Therefore, one could not expect that a reaction proceeds in the higher yield and selectively also in a compound having the complicated structure and higher reactive carbonyl group and the like in the present invention.

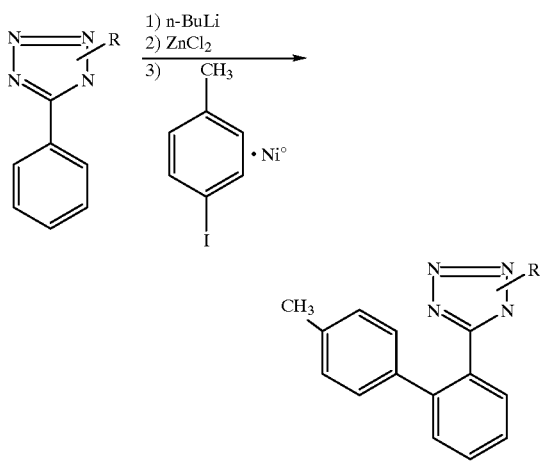

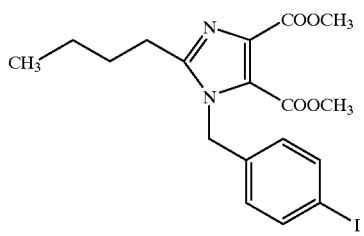

As an inert solvent used in the present invention, any solvent can be used which has no adverse influence on a reaction, for example, DMF, dichloromethane, tetrahydrofuran and the like. The reaction is shown in Reaction Scheme 2. A compound (1) is first dissolved in a suitable solvent such as DMF and the like, the solution is, for example, reacted with 4-halogenobenzyl bromide in the presence of an base such as sodium hydride and the like, ant the reaction is heated at refluxing with hydrazine monohydrate to give a compound (6). The compound (6) is then dissolved in a suitable solvent such as dichloromethane and the like, the solution is, for example, reacted with 1,4-dimethyl-1,3-cyclohexanediene in the presence of an oxidizing agent such as lead tetraacetate and the like to give a compound (7). C ring double bond of the compound (7) is then reduced with a diimide generated by dropping sodium acetate while heating at reflux in the presence of p-toluenesulfonylhydrazine and dimethoxymethane to give a compound (8). Further, for example, phenyltetrazole (10) protected with a suitable protecting group such as triphenylmethyl group and the like is dissolved in a suitable solvent such as tetrahydrofuran and the like, the solution is reacted with n-butyl lithium under cooling and further zinc chloride is added thereto to give arylzinc chloride. This arylzinc chloride is reacted with the compound (8) in the presence of nickel to construct a biphenyltetrazole part. The resulting compound is then is dissolved in a suitable solvent such as tetrahydrofuran and the like, and diisobutylaluminium hydride is added dropwise under cooling to selectively reduce carbonyl at 4-position. Further, a protecting group such as triphenylmethyl group and the like is removed with an acid such as dilute sulfuric acid to give an end compound [I]. In addition, a compound at each reaction step can be purified by silica gel column chromatography and the like, if necessary.

DESCRIPTION OF THE PREFERRED EMBODIMENTS

The following Examples illustrate the present invention in detail.

EXAMPLE 1

Synthesis of 2-butyl-1-(4-iodobenzyl)imidazol-4,5-dicarboxylic acid represented by the chemical formula

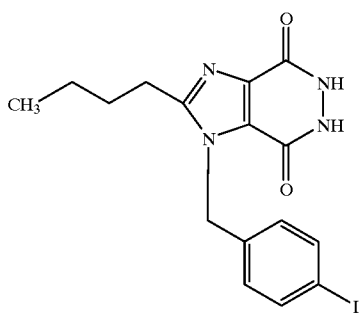

Dimethyl 2-butylimidazol-4,5-dicarboxylic acid (7.12 g, 29.6 mmol) and 4-iodobenzyl bromide (10.56 g, 35.5 mmol) were dissolved in DMF (50 ml), and 60% oily sodium hydride (1.3 g, 32.5 mmol) was added in small portions while stirring at room temperature. The reaction solution was stirred at room temperature for 2 hours and methanol was added to treat excess sodium hydride. Then the reaction solution was neutralized with 2N HCl and the product was extracted with dichloromethane. The extracted solution was dried over sodium sulfate and concentrated in reduced pressure. The residue was purified by silica gel column chromatography (ethyl acetate:hexane=1:1) to give the titled compound (11.1 g, 82%) as a tan solid (mp:98–99° C., Rf:0.60 silica gel-ethyl acetate/hexane/=1/1). This has the following NMR spectrum.

$^1$H-NMR (CDCl$_3$) δ ppm: 0.88 (3H, t, J=7.4 Hz), 1.34 (2H. sex, J=7.4 Hz), 1.66 (2H, qui, J=7.4 Hz), 2.63 (2H, t, J=7.4 Hz), 3.81 (3H, s), 3.92 (3H, s), 5.35 (2H, s), 6.74 (2H, d, J=8.6 Hz), 7.64 (2H, d, J=8.6 Hz)

EXAMPLE 2

Synthesis of 2-butyl-1-(4-iodobenzyl)imidazo[4,5-d]pyridazine-4,(5H),7,(6H)-dione represented by the chemical formula A mixture of dimethyl 2-butyl-1-(4-iodobenzyl)imidazol-4,5-dicarboxylic acid (8.68 g, 19.0 mmol) and hydrazine monohydrate (20 ml) was heated at reflux for 1.5 hours. Excess hydrazine was distilled off under reduced pressure, water (40 ml) was added thereto, the reaction solution was made acidic (pH=1) by addition of 12 N HCl and the solution was cooled on ice. The resulting precipitates were filtered, washed successively with ethanol (40 ml×2) and ether (40 ml×2), the filtered material was dried at 50° C. under vacuum to give a titled compound (8.4 g, 100%) as white powders (mp>250° C., Rf: 0.58 silica gel-chloroform/methanol=10/1). This has the following NMR spectrum.

$^1$H-NMR (DMSO-d$_6$) δ ppm: 0.86 (3H, t, J=7.5 Hz), 1.33 (2H, sex, J=7.5 Hz), 1.66 (2H, qui, J=7.5 Hz), 2.70 (2H, t, J=7.5 Hz), 5.70 (2H, s), 6.97 (2H, d, J=8.4 Hz), 7.66 (2H, d, J=8.4 Hz)

EXAMPLE 3

Synthesis of 2-butyl-5,8-dimethyl-5,8-dihydro-5,8-ethano-1-(4-iodobenzyl)-1H-1,3,4a,8a-tetraazacyclopentanaphthalene-4,9-dione represented by the chemical formula

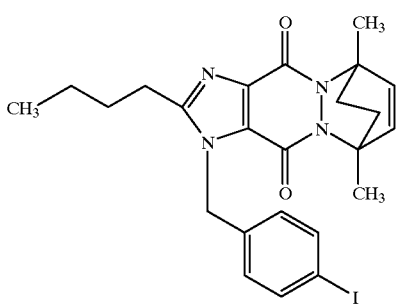

2-Butyl-1-(4iodobenzyl)imidazo[4,5-d]pyridazine-4,(5H),7,(6H)-dione (7.64 g, 18.0 mmol) and 1,4dimethyl-1,3-cyclohexanediene (purity 64%, 4.6 g, 27.3 mmol) were suspended in dichloromethane (150 ml) and the suspension was cooled to −25° C. Lead tetraacetate (purity 91%, 26.3 g, 54.0 mmol) was added in small portions. The temperature of the reaction mixture was returned slowly to 0° C. to react for 2.5 hours. Toluene (100 ml) was added and the resulting precipitates were filtered and washed with dichloromethane. The filtrate and washes were combined and concentrated under reduced pressure and the residue was purified by silica gel column chromatography (ethyl acetate) to give a titled compound (7.65 g, 80%) as pale-yellow powders (mp: 157–158° C., Rf: 0.51 silica gel-ethyl acetate). This has the following NMR spectrum.

$^1$H-NMR (CDCl$_3$) δ ppm: 0.86 (3H, t, J=7.5 Hz), 1.31 (2H, sex, J=7.5 Hz), 1.61 (2H, m), 1.69 (2H, qui, J=7.5 Hz), 2.13 (3H, s), 2.21 (3H, s), 2.61 (2H, t, J=7.5Hz), 5.59 (2H, AB, JAB=16 Hz), 6.36 (2H, AB, JAB=16 Hz), 6.81 (2H, d, J=8.4 Hz), 7.64 (2H, d, J=8.4 Hz)

EXAMPLE 4

Synthesis of 2-butyl-5,8-dimethyl-5,8-ethano-1-(4iodobenzyl)-5,6,7,8-tetrahydro-1H-1,3,4a,8a-tetraazacyclopentanaphthalene-4,9-dione 2-Butyl-5,8-dimethyl-5,8-dihydro-5,8-ethano-1-(4iodobenzyl)-1H-1,3,4a,8a-tetraazacyclopentanaphthalene-4,9-dione (3 g, 5.66 mmol) and p-toluenesulfonylhydrazine (8.4 g, 45.1 mmol) were dissolved in DMF (16 ml) and the solution was heated to reflux. A solution obtained by dissolving sodium acetate (7.4 g, 90.2 mmol) in water (16 ml) was added dropwise slowly over 3 hours. The solvent was distilled off under reduced pressure, the residue was dissolved in dichloromethane, washed with water, dried over sodium sulfate and concentrated under reduced pressure. The residue was washed with hexane and dried at 45° C. under vacuum to give a titled compound (2.6 g, 87%) as white powders (mp: 208–209° C., Rf: 0.51 silica gel-ethyl acetate). This has the following NMR spectrum.

$^1$H-NMR (CDCl$_3$) δ ppm: 0.87 (3H, t, J=7.5 Hz), 1.33 (2H, sex, J=7.5 Hz), 1.61–1.76 (6H, m), 1.81 (3H, s), 1.89 (3H, s), 2.17 (4H, m), 2.64 (2H, t, J=7.5 Hz), 5.61 (2H, s) 6.83 (2H, d, J=7.1 Hz), 7.65 (2H, d, J=7.1 Hz)

EXAMPLE 5

Synthesis of 2-butyl-5,8-dimethyl-5,8-ethano-5,6,7,8-tetrahydro-1-[[2'-(1-triphenylmethyl-1H-tetrazol-5-yl)-4biphenyl]methyl]-1H-1,3,4a,8a-tetraazacyclopentanaphthalene-4,9-dione represented by the chemical formula 4Phenyl-1-triphenylmethyl-1H-tetrazole (365 mg, 0.94 mmol) was dissolved in THF (2 ml), the solution was cooled to −20° C. and a 1.6 M solution of n-butyl lithium in hexane (0.7 ml, 1.12 mmol) was added dropwise while stirring under nitrogen atmosphere. The temperature of this solution was raised from −20° C. to −10° C. over 1 hour and the solution was stirred for a further 30 minutes. A suspension of zinc chloride (153 mg, 1.12 mmol) in THF (1 ml) was added thereto and the reaction was warmed to 0° C. to give arylzinc chloride.

In a separate vessel, bis(triphenylphosphine)nickel (II) dichloride (62.9 mg, 0.096 mmol) was suspended in THF (1 ml) under nitrogen atmosphere, and a 1M solution of methylmagnesium chloride in THF (0.2 ml, 0.2 mmol) was added thereto at room temperature. Then a solution of 2-butyl-5,8-dimethyl-5,8-ethano-1-(iodobenzyl)-5,6,7,8-tetrahydro-1H-1,3,4a,8a-tetraazacyclopentanaphthalene-4,9-dione (250 mg, 0.47 mmol) in THF (6 ml) and a solution of arylzinc chloride in THF as prepared above were added thereto successively. The reaction mixture was stirred at room temperature for 10 hours, acetic acid (0.2 ml) was added to stir for 30 minutes, a saturated aqueous solution of sodium chloride (2 ml) was added to stir for another 30 minutes, and the mixture was allowed to stand to separate THF layer and aqueous layer. The THF layer was taken, the aqueous layer was extracted with THF (5 ml), the THF layers were combined, washed with 28% ammonia solution in water (3 ml), dried over sodium sulfate and concentrated under reduced pressure. The residue was purified by silica gel column chromatography to give a titled compound (289 mg, 77.4%) as white powders.

EXAMPLE 6

Synthesis of 2-butyl-5,8-dimethyl-5,8-ethano-5,6,7,
8-tetrahydro-1-[[2'-(1-triphenylmethyl-1H-tetrazol-
5-yl)-4-biphenyl]methyl]-1H,4H-1,3,4a,8a-
tetraazacyclopentanaphthalene-9-one represented by
the chemical formula

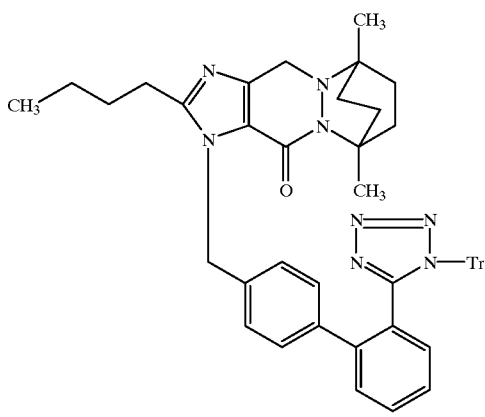

2-Butyl-5,8-dimethyl-5,8-ethano-5,6,7,8-tetrahydro 1-[[2'-(1-triphenylmethyl-1H-tetrazol-5-yl)-4biphenyl] methyl]-1H-1,3,4a,8a-tetraazacyclopentanaphthalene-4,9-dione (93,1 g, 0.12 mmol) was dissolved in THF (1.2 l) while warming, the solution was cooled to −45° C., and a solution of DIBAH (1.5 M solution in toluene, 230 ml, 0.35 mol) was slowly added dropwise under nitrogen atmosphere. The mixture was stirred at the same temperature for 1 hour, a saturated aqueous solution of sodium chloride was added and the mixture was warmed to room temperature. The organic layer was decanted, the precipitates were washed with ethyl acetate, combined with the above organic layer and the mixture was dried over sodium sulfate. The solvent was distilled off under reduced pressure to give a titled compound (96.6 g) as pale yellow solid. This has the following NMR spectrum.

$^1$H-NMR (CDCl$_3$) δ ppm: 0.82 (3H, t, J=7.2 Hz), 1.14 (3H, s), 1.20–1.31 (2H, m),149–168 (6H, m), 1.71 (3H, s), 2.04–2.14 (4H, m), 2.43 (2H, t, J=8.0 Hz), 3.98 (2H, s), 5.46 (2 H, s) 6.89–7.51 (22H, m), 7.88 (1H, dd, J=1.5, 7.5 Hz)

EXAMPLE 7

Synthesis of 2-butyl-5,8-dimethyl-5,8-ethano-5,6,7,
8-tetrahydro-1-[[2'-(1H-tetrazol-5-yl)-4biphenyl]
methyl]-1H,4H-1,3,4a,8a-
tetraazacyclopentanaphthalene-9-one represented by
the chemical formula

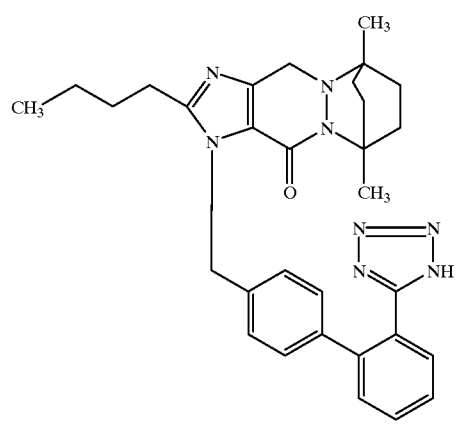

2-Butyl-5,8-dimethyl-5,8-ethano-5,6,7,8-tetrahydro-1-[[2'-(1-triphenylmethyl-1H-tetrazol-5-yl)-4-biphenyl] methyl]-1H,4H-1,3,4a,8a-tetraazacyclopentanaphthalene-9-one (96.3 g) was dissolved in acetone (720 ml), 2N HCl (220 ml) was added thereto and the mixture was heated to stir at 55° C. for 30 minutes. The reaction mixture was cooled to 0° C., a saturated aqueous solution of sodium chloride was added to adjust to pH 4, acetone was distilled off under reduced pressure and the resulting aqueous layer was extracted with methylene chloride. The organic layer was washed successively with water and saturated aqueous solution of sodium chloride and dried over sodium sulfate. The solvent was distilled off under reduced pressure, the resulting residue was purified by silica gel column chromatography (chloroform-chloroform/methanol=50/1) to give a titled compound (53.5 g, 91%, 2st eps) as pale yellow solid. This has the following NMR spectrum.

$^1$H-NMR (CDCl$_3$) δ ppm: 0.84 (3H, t, J=7.2 Hz), 1.01 (3H, s), 1.22–1.36 (2H, m), 151–1.69 (6H, m), 1.58 (3H, s), 1.89–2.01 (4H, m), 2.41 (2H, t, J=7.7 Hz), 3.63 (2H, s), 5.43 (2H, s), 6.91 (2H, d, J=8.0 Hz), 7.05 (2H, d, J=8.0 Hz), 7.44–7.65 (3H, m), 7.87 (1H, d, J=6.8 Hz)

We claim:
1. A process for producing a compound represented by the chemical formula:

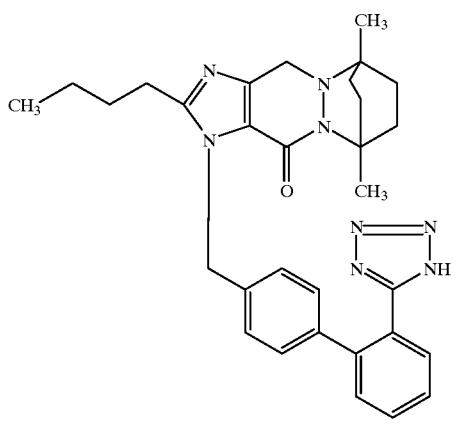

or a pharmacologically acceptable salt thereof which comprises:

reacting a compound represented by the chemical formula:

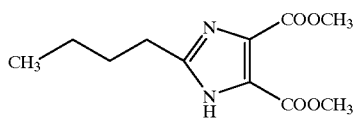

with 4-iodobenzyl or 4-bromobenzyl-bromide and subsequently with hydrazine to give a compound represented by the chemical formula:

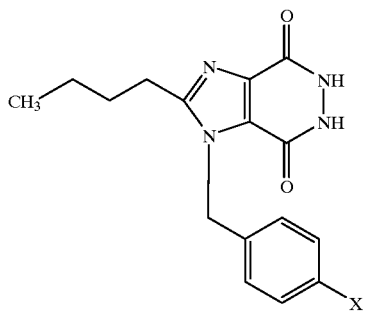

wherein X represents bromine or iodine,
reacting the above compound with 1,4-dimethyl-1,3-cyclohexanediene in the presence of lead tetra-acetate, subjecting the newly generated double bond of the formula:

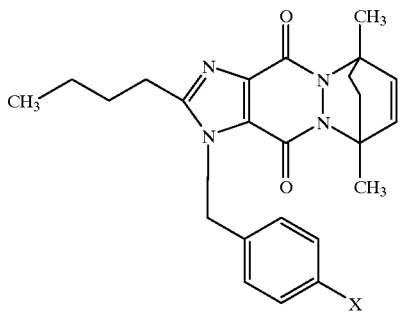

to catalytic or diimide reduction and subsequently to diisobutylaluminium hydride reduction to give a compound represented by the chemical formula:

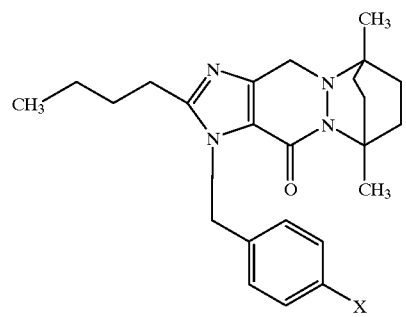

wherein X represents bromine or iodine, and reacting the above compound with a compound represented by the general formula:

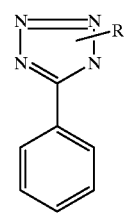

wherein R represents hydrogen, sodium, potassium, alkyl group or optionally substituted aryl group and when R is other than hydrogen removal of R groups to give

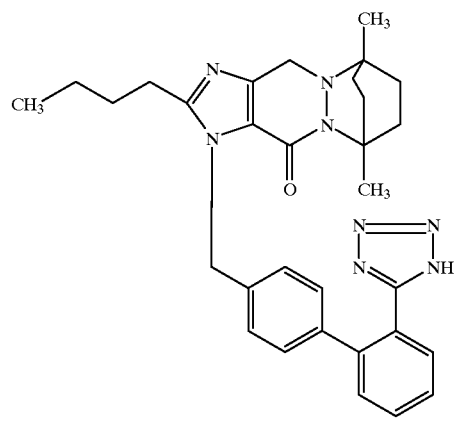

2. A process for producing a compound represented by the chemical formula:

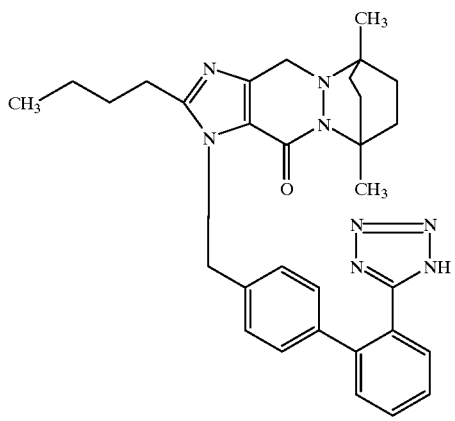

or a pharmacologically acceptable salt thereof which comprises:

reacting a compound represented by the chemical formula:

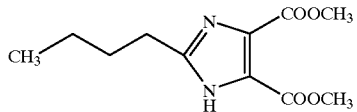

with 4-iodo benzyl or 4-bromobenzyl bromide and subsequently with hydrazine to give a compound represented by the chemical formula:

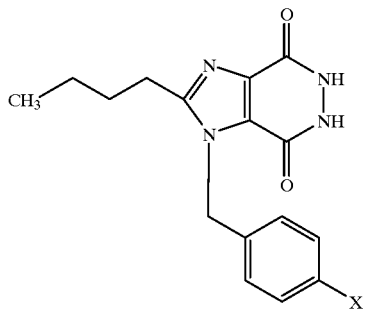

wherein X represents bromine or iodine, reacting the above compound with 1,4-dimethyl-1,3-cyclohexanediene in the presence of lead tetra-acetate, subjecting the newly generated double bond of the formula:

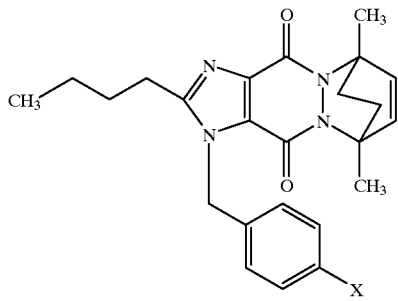

to catalytic or diimide reduction to give a compound represented by the chemical formula:

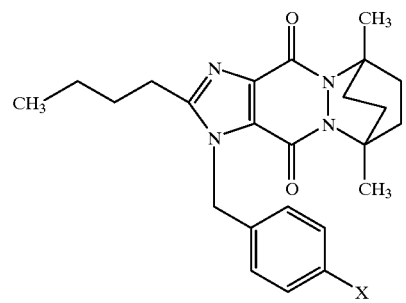

wherein X represents bromine or iodine, reacting the above compound with a compound represented by the chemical formula:

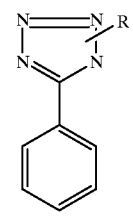

wherein R represents hydrogen, sodium, potassium, alkyl group or optionally substituted aryl group, and subjecting the resulting compound to diisobutylaluminium hydride reduction and when R is other than hydrogen removal of R groups to give

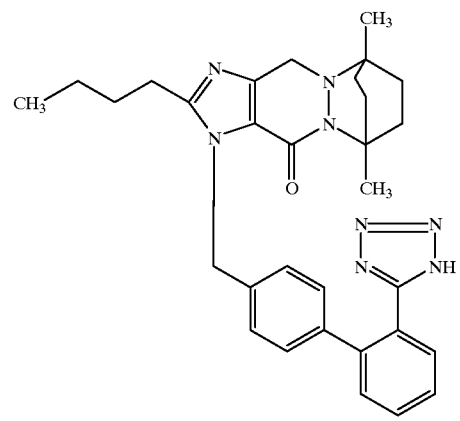

* * * * *